United States Patent [19]

Rizkalla

[11] 4,115,444
[45] Sep. 19, 1978

[54] PROCESS FOR PREPARING CARBOXYLIC ACID ANHYDRIDES

[75] Inventor: Nabil Rizkalla, River Vale, N.J.

[73] Assignee: Halcon International, Inc., New York, N.Y.

[21] Appl. No.: 654,661

[22] Filed: Feb. 5, 1976

Related U.S. Application Data

[63] Continuation-in-part of Ser. No. 556,750, Mar. 10, 1975.

[51] Int. Cl.$^2$ .............. C07C 53/12; C07C 53/26; C07C 63/04
[52] U.S. Cl. ........................... 260/549; 260/546
[58] Field of Search ........................ 260/546, 549

[56] References Cited

U.S. PATENT DOCUMENTS

| | | | |
|---|---|---|---|
| 2,730,546 | 1/1956 | Reppe et al. | 260/546 |
| 2,789,137 | 4/1957 | Reppe et al. | 260/546 |
| 3,717,670 | 2/1973 | Schultz | 260/476 |
| 3,819,669 | 6/1974 | Knifton | 260/410.9 |
| 3,821,265 | 6/1974 | Forster et al. | 260/413 |
| 3,856,856 | 12/1974 | Nozaki | 260/532 |
| 3,892,788 | 1/1975 | Knifton et al. | 260/410.9 |
| 3,927,078 | 12/1975 | Lapporte et al. | 260/494 |
| 3,989,751 | 11/1976 | Forster et al. | 260/546 |
| 4,002,677 | 1/1977 | Naglieri et al. | 260/546 |
| 4,002,678 | 1/1977 | Naglieri et al. | 260/546 |
| 4,046,807 | 9/1977 | Kuckertz | 260/549 |

OTHER PUBLICATIONS

Falbe, "CO in Org. Syn", pp. 78–79 (1970).
House, "Modern Synthetic Reactions", 2nd edition, 1972, W. A. Benjamin Inc., Menlo Park, Calif., p. 786.

Primary Examiner—Norman Morgenstern
Attorney, Agent, or Firm—William C. Long; David Dick; Riggs T. Stewart

[57] ABSTRACT

A carboxylic acid anhydride such as acetic anhydride, is prepared from a carboxylate ester or a hydrocarbyl ether in carbonylation processes comprising the use of a halide, carbon monoxide and a Group VIII noble metal in the presence of promoters comprising at least one metal of Groups IVB, VB, and VIB or a non-noble metal of Group VIII, or their compounds and an organo-nitrogen compound or an organo-phosphorus compound wherein the nitrogen and phosphorus are trivalent.

26 Claims, No Drawings

PROCESS FOR PREPARING CARBOXYLIC ACID ANHYDRIDES

CROSS-REFERENCE TO RELATED APPLICATION

This application is a continuation-in-part of co-pending application Ser. No. 556,750, filed Mar. 10, 1975.

This invention relates to the preparation of the anhydrides of carboxylic acids, more particularly mono-carboxylic acids, and especially the anhydrides of lower alkanoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the action of carbon monoxide upon various reactants (carbonylation) have been described, for example, in Reppe et al. U.S. Pat. Nos. 2,729,561, 2,730,546 and 2,789,137. However, such prior proposals involving carbonylation reactions have required the use of very high pressure. Carbonylation at lower pressures has been proposed but as a route to the preparation of acetic acid. French Pat. No. 1,573,130, for example, describes the carbonylation of methanol and mixtures of methanol with methyl acetate in the presence of compounds of iridium, platinum, palladium, osmium and ruthenium and in the presence of bromine or iodide under more moderate pressures than those contemplated by Reppe et al. Similarly, South African Pat. No. 68/2174 produces acetic acid from the same reactants using a rhodium component with bromine or iodide. More recently, Schultz (U.S. Pat. Nos. 3,689,533 and 3,717,670) has disclosed a vapor-phase process for acetic acid production employing various catalysts comprising a rhodium component dispersed on a carrier. None of these relatively recent carbonylation disclosures, however, refers to or contemplates the preparation of acetic anhydride or other carboxylic acid anhydrides.

Improved processes for preparing carboxylic acid anhydrides, including acetic anhydride, are disclosed in co-pending applications of Colin Hewlett Ser. No. 394,220, filed Sept. 4, 1973 and Ser. No. 467,977 filed May 8, 1974, the disclosures of both of which are incorporated herein by reference. In application Ser. No. 467,977 there is disclosed the use of promoters which are elements having atomic weights greater than 5 of Groups IA, IIA, IIIA, IVB, and VIB, the non-noble metals of Group VIII, and the metals of the lanthanide and actinide groups of the Periodic Table, and their compounds.

It is an object of the present invention to provide a further improved process for the manufacture of carboxylic acid anhydrides, especially lower alkanoic anhydrides, such as acetic anhydride.

In accordance with the invention, a carboxylic ester and/or a hydrocarbyl ether are carbonylated under substantially anhydrous conditions in the presence of a Group VIII noble metal catalyst, in the presence of a halide which is an iodide or a bromide and in the presence of promoters comprising at least one metal of Groups IVB, VB and VIB or a non-noble metal of Group VIII, or their compounds, in combination with an organo-nitrogen compound or an organo-phosphorus compound wherein the nitrogen and phosphorus are trivalent. It has been discovered that this catalyst-multiple promoter system amkes possible reduced pressures, especially carbon monoxide partial pressures, lower catalyst concentrations, lower temperatures and shorter contact times. The rate of reaction and the product concentration realized from this catalyst-multiple promoter combination have been found to be exceptionally high. Moreover, it has also been found that the promoters stabilize the catalyst, and inhibit corrosion.

Thus, in accordance with the invention, carbon monoxide is reacted with a carboxylate ester, especially a lower alkyl alkanoate, or a hydrocarbyl ether such as a lower alkyl ether, to produce a carboxylic anhydride, such as a lower alkanoic anhydride, the carbonylation taking place in the presence of an iodide or bromide, e.g., a hydrocarbyl halide, especially a lower alkyl halide, which is an iodide or a bromide, such as methyl iodide. Thus, acetic anhydride, for example, can be effectively prepared in a representative case by subjecting methyl acetate or dimethyl ether to carbonylation in the presence of methyl iodide. In all cases, the carbonylation is carried out under anhydrous conditions in the presence of the catalyst-multiple promoter system described above. As indicated, an ester-ether mixture can be carbonylated if desired.

It will be understood that the hydrocarbyl halide may be formed in situ and the halide may thus be supplied to the system not only as the hydrocarbyl halide but the halogen moiety may also be supplied as another organic halide or as the hydrohalide or other inorganic halide, e.g., salts, such as the alkali metal or other metal salts, or even as elemental iodine or bromide. Following the reaction the organic components of the reaction mixture are readily separated from one another, as by fractional distillation.

In like manner, other lower alkanoic anhydrides, i.e., anhydrides of lower alkanoic acids, such as propionic anhydride, butyric anhydrides and valeric anhydrides, can be produced by carbonylating the corresponding lower alkyl alkanoate or a lower alkyl ether. Similarly, other carboxylic acid anhydrides, e.g., the anhydrides of other alkanoic acids, such as those containing up to 12 carbon atoms, for example capric anhydrides, caprylic anhydrides and lauric anhydrides, and like higher anhydrides are produced by carbonylating the corresponding ester, e.g. alkyl alkanoates containing up to 11 carbon atoms in the alkyl group up to 12 carbon atoms in the carboxylate group, or aryl esters, or the corresponding ether, such as heptyl caprylate, nonyl decanoate, undecyl laurate, phenyl benzoate, heptyl ether, nonyl ether, phenyl ether, and the like.

It is preferred that the reactants be selected so that the resulting anhydride will be a symmetrical anhydride, i.e., having two identical acyl groups, viz., wherein R in equations (1) and (2) is the same in each instance, but it is within the scope of the invention to produce non-symmetrical or mixed anhydrides and this can be readily effected by using different combinations of reactants, e.g., by using compounds having different R groups in the foregoing reactions, as will be obvious to persons skilled in the art.

The above-described reactions can be expressed as follows:

wherein R is a hydrocarbyl radical which may be saturated, e.g., alkyl of 1 to 11 carbon atoms, or monocyclic aryl, e.g., phenyl, or alkaryl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention. The more volatile alkyl halide, by-product acyl halide and unreacted ether or ester in the final produce mixture can be readily removed, as by distillation, for recycling, and the net yield of product is substantially exclusively the desired carboxylic anhydride. In the case of liquid-phase reaction, which is preferred, the organic compounds are easily separated from the metal-containing components, as by distillation. The reaction is suitably carried out in a reaction zone to which the carbon monoxide, the ester or ether, the halide and the noble metal catalyst and the promoters are fed. No water is produced in the above-described reactions and anhydrous or substantially anhydrous conditions are employed.

In carrying out the process of the invention, a wide range of temperatures, e.g., 25° to 350° C are suitable but temperatures of 100° to 250° C are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 1000 p.s.i., and most preferably 30 to 200 p.s.i., although carbon monoxide partial pressure of 1 to 10,000 p.s.i. can also be employed. By maintaining the partial pressure of carbon monoxide at the values specified, adequate amounts of this reactant are always present. The total pressure is preferably that required to maintain the liquid phase and in this case the reaction can be advantageously carried out in an autoclave or similar apparatus. The final reaction mixture will normally contain an acyl halide and a hydrocarbyl halide along with the product anhydride and these halides, after separation from the anhydride, can be recycled to the reaction. At the end of the desired residence time, the reaction mixture is separated into its several constituents, as by distillation. Preferably, the reaction product is introduced into a distillation zone, which may be a fractional distillation column, or a series of columns, effective to separate the hydrocarbyl halide, acyl halide and the ester or ether, free organic promoter and the product anhydride. The boiling points of these several compounds are sufficiently far apart that their separation by conventional distillation presents no particular problem. Likewise, the higher boiling organic components can be readily distilled away from the noble metal catalyst, the metal-containing promoter, and any organic promoter which may be in the form of a relatively non-volatile complex. The hydrocarbyl halide and the noble metal catalyst, as well as the acyl halide and the promoters, can then be combined with fresh amounts of ester or ether and carbon monoxide and reacted to produce additional quantities of anhydride.

The ratio of ester or ether to the halide in the reaction system can vary over a wide range. Typically, there are used 0.1 to 1000 moles of the ester or ether per mole of halide, preferably 1 to 30 moles per mole.

The process is advantageously carried out in the presence of a solvent or diluent, particularly when the reactant has a relatively low boiling point, as in the case of di-methyl ether. The presence of a higher boiling solvent or diluent, which may be the product anhydride itself, e.g., acetic anhydride in the case of di-methyl ether, or which may be the corresponding ester, e.g., methyl acetate, again in the case of methyl ether, will make it possible to employ more moderate total pressure. Alternatively, the solvent or diluent may be any organic solvent which is inert in the environment of the process such as hydrocarbons, e.g., octane, benzene, toluene, or carboxylic acids, e.g., acetic acid, and the like. The carboxylic acid, when used, should preferably correspond to the anhydride being produced. A solvent or diluent is suitably selected which has a boiling point sufficiently different from the desired product in the reaction mixture so that it can be readily separated, as will be apparent to persons skilled in the art.

The Group VIII noble metal catalyst, i.e., iridium, osmium, platinum, palladium, rhodium and ruthenium, can be employed in any convenient form, viz., in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly, complexes of the metals can be employed, for example the metal carbonyls, such as iridium carbonyls and rhodium carbonyls, e.g., hexarhodium hexadecacarbonyl, or as other complexes such as the carbonyl halides, e.g., iridium tri-carbonyl chloride $[Ir(CO)_3Cl]_2$ or chlorodicarbonyl rhodium dimer, or the acetylacetonates, e.g., rhodium acetylacetonate $RH(C_5H_7O_2)_3$. Other suitable forms of the Group VIII noble metal include trichloro trispyridine rhodium, hydrido carbonyl tris(triphenyl phosphine) rhodium, dirhodium octacarbonyl, chlorotris triphenyl phosphine) rhodium, chlorocarbonyl bis(triphenyl phosphine) rhodium, and corresponding forms of other Group VIII noble metals, e.g., corresponding palladium compounds. Included among the catalysts listed above are complexes of the Group VIII noble metal with organic promoter ligands derived from the organic promoters hereinafter described. It will be understood that the foregoing compounds and complexes are merely illustrative of suitable forms of the Group VIII noble metal catalyst and are not intended to be limiting.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. Hydrogen which may be present in very small (trace) amounts as an impurity is not objectionable and even may tend to stabilize the catalyst, but significant amounts may tend to affect radically the character of the products produced during the carbonylation, as disclosed in the commonly assigned application of Nabil Rizkalla and C. N. Winnick entitled "Process for Preparing Ethylidene Diacetate"(attorney docket number 1086A) being filed on even date herewith, the disclosure of which is incorporated herein by reference.

In accordance with the invention, the activity of the Group VIII noble metal catalysts described above is significantly improved, particularly with respect to reaction rate and product concentration, catalyst stability and corrosion inhibition, by the concurrent use of a promoter combination or co-promoter system containing a metal component which is a metal of Groups IVB, VB and VIB, and the non-noble metals of Group VIII in association or combination with an organo-nitrogen compound or an organo-phosphorus compound wherein the nitrogen and the phosphorus are trivalent. In the case of the metal component, particularly preferred are the lower atomic weight metals of each of these groups, e.g., those having atomic weights lower than 100, and especially preferred are the metals of Group VIB, and the non-noble metals of Group VIII. In general, the most suitable elements are chromium, iron, cobalt and nickel. Most preferred is chromium. The promoters may be used in their elemental form, e.g., as finely-divided or powdered metals, or they may be employed as compounds of various types, both organic and inorganic, which are effective to introduce the element into the reaction system. Thus, typical compounds of the promoter elements include oxides, hydroxides, halides, e.g., bromides and iodides, oxyhalides, hydrides, alkoxides, and the like. Especially preferred organic-metal compounds are the salts of organic mono-carboxylic acids, e.g., alkanoates such as acetates, butyrates, decanoates, laurates, benzoates, and the like. Other compounds include the metal alkyls and carbonyl compounds as well as chelates, association compounds and enol salts. Particularly preferred are the elemental forms, compounds which are bromides or iodides, and organic salts, e.g., salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g., as a finely-divided metal, a slight induction period is observed.

The metals employed may contain impurities normally associated with the commercially available metal or metal compounds, and need not be purified any further. Thus, the commercially available metal or metal compound is suitably employed in the case of the Group VIII noble metal catalyst and in the case of the metal promoter.

The organic co-promoter can, in its broader sense, be any organo-nitrogen or organo-phosphorus compound wherein the nitrogen and phosphorus are trivalent. Preferably, however, the organo-nitrogen co-promoter is an amine, especially a tertiary amine of the formula

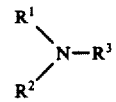

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine, tetraacetic acid, and the like, or a heterocyclic amine such as pyridine, picoline, quinoline, methylquinoline, hydroxy quinoline, pyrrole, pyrrolidine, pyrrolidone, and the like, or an inidazole, such as imidazole, methyl imidazole and the like, or an imide of a carboxylic acid which may be monobasic or polybasic and which may be aliphatic or aromatic and preferably contain up to 20 carbon atoms, such as acetic acid, succinic acid, phthalic acid, pyromellitic acid, e.g. N,N-dimethylacetamide, succinimide, phthalimide and pyromellitic diimide, or a nitrile or amide which may be aliphatic or aromatic and preferably contain up to 20 carbon atoms, e.g., acetonitrile, hexamethyl phosphoric triamide, and like imides, nitriles, and amides, or an oxime such as cyclohexanone oxime, and the like. It will be understood, however, that higher molecular weight promoters e.g., polymeric forms of the organo-nitrogen compounds, may be used such as polyvinylpyridine, polyvinyl pyrrolidone, and the like.

The organo-phosphorus co-promoter is preferably a phosphine of the formula

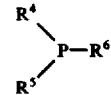

wherein $R^4$, $R^5$ and $R^6$ may be the same or different and are alkyl, cycloalkyl, aryl groups, amide groups or halogen atoms, preferably containing up to 1 to 20 carbon atoms in the case of alkyl and cycloalkyl groups and 6 to 18 carbon atoms in the case of aryl groups. Typical phosphines include trimethylphosphine, tripropylphosphine, tricyohexylphosphine and triphenylphosphine.

Although it is preferred that the organic promoters be added separately to the catalyst system, it is possible to add them as complexes with the Group VIII noble metal such as the trichloro trispyridine rhodium, tris(triphenyl phosphine) rhodium, chlorotris(triphenyl phosphine) rhodium, and chlorocarbonyl bis (triphenyl phosphine) rhodium previously mentioned. Both free organic promoters and complexed promoters can also be used. Indeed, when a complex of the organic promoter and the Group VIII noble metal is used, it is desirable to add free organic promoter as well.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester or ether, preferably 1 mol per 100 to 10,000 mols of ester or ether, and most preferably 1 mol per 500 to 2000 mols of ester or ether.

The quantity of metal promoter can vary widely. Typically, it is one mole per 10,000 moles of ester or ether, preferably it is used in the amount of 1 mole per 20 to 2000 moles, most preferably 1 mole per 50 to 500 moles of ester or ether. The quantity of organic promoter can also vary widely but typically it is used in the amounts of 1 mole per 1 to 10,000 moles of ester or ether, preferably 1 mole per 10 to 1000, most preferably 15 to 200 moles of ester or ether.

In the working up of the reaction mixtures, e.g., by distillation, as discussed above, the metal promoter generally remains with the Group VIII noble metal catalyst, i.e., as one of the least volatile components, and is suitably recycled or otherwise handled along with the catalyst. The organic promoter can also be recovered and recycled.

It will be apparent that the above-described reactions lend themselves readily to continuous operation in which the reactants and catalyst, preferably in combination with the promoter combination are continuously supplied to the appropriate reaction zone and the reaction mixture continuously distilled to separate the volatile organic constituents and to provide a net product consisting essentially of carboxylic acid anhydride, with the other organic components being recycled and, in the case of liquid-phase reaction, a residual Group VIII noble metal-containing (and promoter-containing) fraction also being recycled. In the case of such continuous operation, it will be apparent that the halogen moiety remains in the system at all times subject only to occasional handling losses or purges. The small amount of halogen makeup which may be needed from time to time is preferably effected by supplying the halogen in the form of the hydrocarbyl halide but, as pointed out above, the halogen moiety may also be supplied as another organic halide or as the hydrogen halide or other inorganic halide, e.g., salts, such as the alkali metal or other metal salts, or as elemental iodine or bromine.

As previously indicated, the carbonylation reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, the catalyst and promoter, i.e., the catalyst components, may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst, or the catalyst and promoter, followed by drying. Catalyst component concentrations upon the carrier may vary widely, e.g., 0.01 weight percent to 10 weight percent, or higher. The organic promoter can be either fed with the reactants or complexed with the catalyst. Typical operating conditions for vapor-phase operation are a temperature of 100° to 350° C, preferably 150° to 275° and most preferably 175° to 255° C, a pressure of 1 to 5000 p.s.i.a., preferably 50 to 1500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4000 hr.$^{-1}$ (STP).

The following examples will serve to provide a fuller understanding of the invention, but it is to be understood that they are given for illustrative purposes only, and are not to be construed as limitative of the invention. In the examples, all parts and percentages are by weight, unless otherwise indicated.

In the examples, the various reactants and catalyst components are charged to the reaction vessel which is then closed and brought to the reaction temperature indicated. The initial carbon monoxide partial pressure specified is the calculated value at reaction temperature at the beginning of the reaction, i.e., at zero conversion. The total pressure is maintained by introducing additional carbon monoxide as the reaction proceeds.

EXAMPLE I

Methyl acetate (350 parts), rhodium trichloride hydrate (2.25 parts), methyl iodide (57 parts), pyridine (15 parts), chromium hexacarbonyl (7.5 parts) and acetic acid (90 parts) were heated at 175° C in a stirred Hastelloy pressure vessel, under an atmosphere of carbon monoxide (continuous total pressure 350 p.s.i.g.; initial partial pressure of carbon monoxide 66 p.s.i.). GC analysis of the reaction mixture after one-hour reaction time showed it to contain 54% acetic anhydride (331 parts).

EXAMPLE II

Methyl acetate (350 parts), rhodium trichloride hydrate (0.2 parts), pyridine (15 parts), methyl iodide (114 parts), chromic iodide (15 parts) and acetic acid (90 parts) were heated at 175° C in a stirred Hastelloy pressure vessel, under an atmosphere of carbon monoxide (continuous total pressure 350 p.s.i.g.; initial carbon monoxide partial pressure 66 p.s.i.). GC analysis of the reaction mixture after one-hour reaction time showed it to contain 26% acetic anhydride (160 parts).

EXAMPLE III

Methyl acetate (300 parts), rhodium trichloride hydrate (2 parts), pyridine (13 parts), methyl iodide (50 parts), and chromium hexacarbonyl (6.4 parts) were heated at 175° C in a stirred Hastelloy-lined autoclave under an atmosphere of carbon monoxide (total pressure 350 p.s.i.g.; initial carbon monoxide partial pressure 65 p.s.i.). After 1-½ hours reaction time a GC analysis of the reaction mixture showed it to contain 62.9% acetic anhydride (282 parts).

EXAMPLE IV

Methyl acetate (350 parts), rhodium trichloride hydrate (2.25 parts), methyl iodide (57 parts), 2-picoline (17 parts) and chromium hexacarbonyl (7.5 parts) were heated at 175° C in a stirred Hastelloy pressure vessel, under an atmosphere of carbon monoxide (continuous total pressure 350 p.s.i.g.; initial partial pressure of carbon monoxide 66 p.s.i.). GC analysis of the reaction mixture after one-hour reaction time showed it to contain 72.4% acetic anhydride (383 parts).

EXAMPLE V

Methyl acetate (100 parts), rhodium trichloride hydrate (0.75 parts), methyl iodide (18 parts), methyl imidazole (.5 parts), chromium carbonyl (2.5 parts) and acetic acid (50 parts) were heated at 175° C in a stirred glass lined pressure vessel, under an atmosphere of carbon monoxide (continuous total pressure 350 p.s.i.g.; initial partial pressure of carbon monoxide 66 p.s.i.). GC analysis of the reaction mixture after one-hour reaction time showed it to contain 38.7% acetic anhydride (76 parts).

EXAMPLE VI

Methyl acetate (100 parts), rhodium trichloride hydrate (0.2 part), methyl iodide (36 parts), pyromellitic diimide (5 parts), chromium hexacarbonyl (5 parts) and acetic acid (50 parts) were heated at 175° C in a stirred glass-lined pressure vessel, under an atmosphere of carbon monoxide (continuous total pressure 350 p.s.i.g.; initial partial pressure of carbon monoxide 66 p.s.i.). GC analysis of the reaction mixture after one-hour reaction time showed it to contain 32.4% acetic anhydride (70 parts).

EXAMPLE VII

Methyl acetate (400 parts), rhodium trichloride hydrate (2.25 parts), methyl iodide (57 parts), triphenyl phosphine (10 parts), and chromium hexacarbonyl (7.5 parts) were heated at 175° C in a stirred Hastelloy pressure vessel under an atmosphere of carbon monoxide (continuous total pressure 350 p.s.i.g.; initial partial pressure of carbon monoxide 66 p.s.i.). GC analysis of the reaction mixture after one-hour reaction time showed it to contain 52.7% acetic anhydride (294 parts).

EXAMPLE VIII

Methyl acetate (170 parts), rhodium trichloride hydrate (one part), methyl iodide (25 parts), succinimide (6.5 parts), chromium carbonyl (3.2 parts), and acetic acid (16 parts) were heated at 175° C in a stirred glass-lined pressure vessel under an atmosphere of carbon monoxide (continuous total pressure 350 p.s.i.g.; initial CO partial pressure 66 p.s.i.). GC analysis of the reaction mixture after one-hour reaction time showed it to contain 40% acetic anhydride (99 parts).

EXAMPLE IX

Methyl acetate (173 parts), rhodium trichloride hydrate (1 part), methyl iodide (25 parts), chromium carbonyl (3.3 parts) and triethylamine (7.5 parts) were heated at 175° C in a stirred Hastelloy pressure vessel under an atmosphere of carbon monoxide (continuous total pressure 350 p.s.i.g.; initial CO partial pressure 66 p.s.i.). GC analysis of the reaction mixture after one-hour reaction time showed it to contain 32% acetic anhydride (76 parts).

EXAMPLE X

Methyl acetate (173 parts), rhodium trichloride hydrate (1 part), methyl iodide (25 parts), chromium carbonyl (3.3 parts), and tri-n-butyl phosphine (17 parts) were heated at 175° C in a stirred Hastelloy pressure vessel under an atmosphere of carbon monoxide (continuous total pressure 350 p.s.i.g.; initial partial pressure 66 p.s.i.). GC analysis of the reaction mixture after one-hour reaction time showed it to contain 56% acetic anhydride (147 parts).

EXAMPLE XI

Example X was repeated, using 22 parts of triphenyl phosphine instead of the tri-n-butyl phosphine. GC analysis of the reaction mixture after one-hour reaction time showed it to contain 53% acetic anhydride (128 parts).

EXAMPLE XII

Dimethyl ether (109 parts), methyl acetate (175 parts), rhodium trichloride hydrate (2 parts), methyl iodide (50 parts), 3-picoline (15 parts), and chromium carbonyl (7.5 parts) were heated at 150° C in a stirred Hastelloy-C pressure vessel under an atmosphere of carbon monoxide, (total pressure 1000 p.s.i.g., CO partial pressure 320 p.s.i.). After 3 hours reaction time, GC analysis of the reaction mixture shows it to contain 50.6% acetic anhydride (242 parts) and 29.3% methyl acetate (140 parts).

EXAMPLE XIII

Methyl acetate (350 parts), rhodium trichloride hydrate (2 parts), methyl iodide (50 parts), acetic acid (90 parts), phthalimide (28 parts) and chromium hexacarbonyl (7.5 parts) were heated at 175° C in a stirred Hastelloy-C pressure vessel under an atmosphere of carbon monoxide (total pressure 350 p.s.i.g.; initial partial pressure of carbon monoxide 70 p.s.i.). After 1 hour reaction time, GC analysis of the reaction mixture shows it to contain 33.3% acetic anhydride (193 parts).

EXAMPLE XIV

Methyl acetate (350 parts), rhodium trichloride hydrate (2 parts), methyl iodide (50 parts), acetic acid (90 parts), 2,6 lutidine (20 parts), and chromium hexacarbonyl (7.5 parts) were heated at 175° C in a stirred Hastelloy-C pressure vessel under an atmosphere of carbon monoxide (total pressure 350 p.s.i.g.; initial partial pressure of carbon monoxide 70 p.s.i). After 1 hour reaction time, GC analysis of the reaction mixture shows it to contain 45.2% acetic anhydride (268 parts).

What is claimed is:

1. In a process for the preparation of an anhydride of a monocarboxylic acid by reacting carbon monoxide, a halide which is an iodide or bromide and a compound selected from the group consisting of a carboxylate ester and a hydrocarbyl ether, under substantially anhydrous conditions in the presence of a Group VIII noble metal catalyst the improvement which comprises carrying out the reaction in the presence of a multiple promoter comprising (1) at least one metal of Group VIB or a non-noble metal of Group VIII and (2) an organo-nitrogen compound or an organo-phosphorus compound wherein the nitrogen and the phosphorus are trivalent.

2. A process as defined in claim 1, wherein the Group VIII noble metal is rhodium.

3. A process as defined in claim 1, wherein the Group VIII noble metal is iridium.

4. A process as defined in claim 1, wherein the halide is a hydrocarbyl halide.

5. A process as defined in claim 1, wherein the metal component of the multiple promoter is a metal of Group VIB or a non-noble metal of Group VIII.

6. A process as defined in claim 1, wherein the metal component of the multiple promoter is selected from the group consisting of chromium, iron, cobalt and nickel.

7. A process as defined in claim 1, wherein the metal component of the multiple promoter is chromium.

8. A process as defined in claim 1, wherein the organo-nitrogen compound component of the multiple promoter is selected from the group consisting of an amine, an imidazole, an imide, a nitrile, an amide and an oxime and the organo-phosphorus compound component of the multiple promoter is a phosphine.

9. In a process for the preparation of a lower alkanoic anhydride by reacting carbon monoxide, a halide which is an iodide or a bromide, and a compound selected from the group consisting of a lower alkyl lower alkanoate and a lower alkyl ether, under substantially anhydrous conditions in the presence of a Group VIII noble metal catalyst, the improvement which comprises carrying out the reaction in the presence of a multiple promoter comprising (1) at least one metal of Group VIB or a non-noble metal of Group VIII and (2) an organo-nitrogen compound or an organo-phosphorus compound wherein the nitrogen and the phosphorus are trivalent.

10. A process as defined in claim 9, wherein the Group VIII noble metal is rhodium.

11. A process as defined in claim 9, wherein the Group VIII noble metal is palladium.

12. A process as defined in claim 9, wherein the halide is a hydrocarbyl halide.

13. A process as defined in claim 9, wherein the metal component of the multiple promoter is a metal of Group VIB or a non-noble metal of Group VIII.

14. A process as defined in claim 9, wherein the metal component of the multiple promoter is selected from the group consisting of chromium, iron, cobalt and nickel.

15. A process as defined in claim 9, wherein the metal component of the multiple promoter is chromium.

16. A process as defined in claim 9, wherein the organo-nitrogen compound component of the multiple promoter is selected from the group consisting of an amine, an imidazole, an imide, a nitrile, an amide and an oxime and the organo-phosphorus compound component of the multiple promoter is a phosphine.

17. In a process for the preparation of acetic anhydride by reacting carbon monoxide, a halide which is an iodide or a bromide and a compound slected from the group consisting of methyl acetate and dimethyl ether, under substantially anhydrous conditions in the presence of a Group VIII noble metal, the improvement which comprises carrying out the reaction in the presence of a multiple promoter comprising (1) at least one metal of Group VIB or a non-noble metal of Group VIII and (2) an organo-nitrogen compound or an organo-phosphorus compound wherein the nitrogen and the phosphorus are trivalent.

18. A process as defined in claim 17, wherein the Group VIII noble metal is rhodium.

19. A process as defined in claim 17, wherein the Group VIII noble metal is iridium.

20. A process as defined in claim 17, wherein the halide is a hydrocarbyl halide.

21. A process as defined in claim 17, wherein the metal component of the multiple promoter is a metal Group VIB or a non-noble metal of Group VIII.

22. A process as defined in claim 17, wherein the metal component of the multiple promoter is selected from the group consisting of chromium, iron, cobalt and nickel.

23. A process as defined in claim 17, wherein the metal component of the multiple promoter is chromium.

24. A process as defined in claim 17, wherein the organo-nitrogen compound component of the multiple promoter is selected from the group consisting of an amine, an imidazole, an imide, a nitrile, an amide and an oxime and the organo-phosphorus compound component of the multiple promoter is a phosphine.

25. A process as defined in claim 17, wherein the Group VIII noble metal is palladium.

26. A process as defined in claim 1, wherein the Group VIII noble metal is palladium.

* * * * *